United States Patent [19]

Haber

[11] Patent Number: 4,634,443

[45] Date of Patent: Jan. 6, 1987

[54] SINGLE CIRCUIT ELASTOFLUIDIC SPHINCTER

[75] Inventor: Terry M. Haber, Lake Forest, Calif.

[73] Assignee: Habley Medical Technology Corporation, Laguna Hills, Calif.

[21] Appl. No.: 752,137

[22] Filed: Jul. 5, 1985

[51] Int. Cl.[4] .................. A61F 2/08; A61B 19/00
[52] U.S. Cl. ..................... 623/14; 128/1 R; 128/DIG. 25
[58] Field of Search ............... 128/1 R, 346, DIG. 25, 128/327, 774, 780, 79; 623/14

[56] References Cited

U.S. PATENT DOCUMENTS

| | | | |
|---|---|---|---|
| 1,810,027 | 6/1931 | Moran et al. | 128/327 |
| 2,271,927 | 2/1942 | Saighman | 128/327 |
| 4,019,499 | 4/1977 | Fitzgerald | 128/1 R |
| 4,222,377 | 9/1980 | Burton | 128/DIG. 25 X |
| 4,419,985 | 12/1983 | Trick | 128/DIG. 25 X |
| 4,549,531 | 11/1985 | Trick | 128/1 R |
| 4,551,862 | 11/1985 | Haber | 128/1 R X |
| 4,571,749 | 2/1986 | Fischell | 128/1 R X |

Primary Examiner—Richard J. Apley
Assistant Examiner—Alan W. Cannon
Attorney, Agent, or Firm—Morland C. Fischer

[57] ABSTRACT

A gastrointestinal sphincter to be surgically implanted around a lumen (e.g. bowel) of a patient to apply variable occlusive pressures for articulating the lumen. The sphincter includes an occlusion cuff having a hollow, expansible chamber formed therein to embrace the lumen. Communicating in a single, continuous fluid circuit with the expansible chamber are first and second fluid circuits having respective reservoir supplies of fluid located therein. Each of the reservoir supplies may be selectively actuated in order that fluid will be delivered to the expansible chamber to controllably expand the chamber and thereby produce variable occlusive pressure levels for achieving coaptive continence. A fluid filled physician control port is interconnected with one of the fluid circuits and surgically implanted so as to be accessible to a fluid filled syringe. A carefully controlled volume of fluid from the port can be delivered to the expansible chamber via the associated fluid path to generate the minimum increased occlusive pressure necessary to achieve coaptive continence according to the tissue requirements of the patient.

19 Claims, 10 Drawing Figures

SINGLE CIRCUIT ELASTOFLUIDIC SPHINCTER

BACKGROUND OF THE INVENTION

1. Field of the Invention

This invention relates to a gastrointestinal sphincter for surgical implantation to surround and embrace a patient's lumen (e.g. bowel) for articulating the lumen by means of a single, continuous fluid circuit by which variable occlusive pressures can be selectively and controllably generated for achieving coaptive continence.

2. Prior Art

Cancer of the colon typically occurs in the rectosigmoidal area of a patient. Halting the spread of such cancer frequently requires a colostomy during which the sphincter ani muscle is surgically excised. While the patient's bowel remains intact, there is no longer an associated sphincter muscle to hold the patient continent and control the movement of fecal material through the bowel. In such a case, the surgeon usually extends the patient's colon to a location outside the stomach. A mouth portion or stoma is formed at the external colon end and a bag is attached thereto to receive fecal material.

The corresponding arrangement of tubes and external valves which are needed to form the stoma end of the colon are often irritating to the patient. Moreover, externally worn bags are generally cumbersome in that they are subject to either changing or replacement, thereby increasing costs and/or subjecting the patient to a possible unsanitary environment. What is more, external belts, adhesives, and the like are typically required to secure the external bag to the body of the patient. Therefore, not only is the patient's mobility limited but the externally worn bag has been known to become separated from the patient. Moreover, the wearer of such externally worn bags sometimes requires assistance in attaching or removing the bag.

The best psychological and physiological treatment of a colostomy patient is to repair and artificially replace internal tissue so that the anal orifice terminates at its presurgery location. However, the artificial sphincter mechanisms heretofore available are not ideally suitable to reliably accomplish the foregoing.

Examples of conventional sphincteric mechanisms can be found be referring to one or more of the following U.S. patents: Nos.

3,863,622 Feb. 4, 1975
4,222,377 Sept. 16, 1980
4,386,601 June 7, 1983
4,417,567 Nov. 29, 1983
4,419,985 Dec. 13, 1983

SUMMARY OF THE INVENTION

Briefly, and in general terms, an elastofluidic, gastrointestinal sphincter is disclosed for surgical implantation around a patient's lumen, such as the bowel. The sphincter includes a continence producing occlusion cuff which is positioned around the bowel to achieve coaptation for the treatment of incontinence. The occlusion cuff includes a hollow, expansible patient actuated chamber arranged to embrace the bowel and generate diametric occlusive pressures for reliably occluding the bowel with a precise and minimal pressure. Communicating with the hollow chamber in a single continuous fluid circuit are first and second fluid paths. Each fluid path includes a fluid filled reservoir and a flow control check valve. The reservoirs are implanted at a manually accessible location of the body to permit the patient to locate and actuate one or both reservoirs and thereby cause fluid to be delivered via respective fluid paths to the expansible chamber to cause a corresponding inflation thereof. Since each of the reservoirs may be selectively actuated to deliver a fluid supply to inflate the expansible chamber, the occlusion cuff is adapted to produce variable occlusive pressure levels for achieving coaptive continence. A fluid filled physician control port communicates with one of the first or second fluid paths. The port is implated so as to be accessible to a fluid filled syringe. In the event that the occlusive pressures generated by means of the patient actuated fluid reservoirs are insufficient to achieve coaptation, the physician may continuously and accurately increase the application of occlusive pressure to the bowel by inserting a syringe into the physician control port so as to supply additional fluid to further inflate the occlusion cuff chamber. Thus, by virtue of the present invention, the physician may selectively adjust the total occlusive forces being generated for achieving coaptive continence without subjecting the patient to additional surgery, so that the sphincter can be individually customized to generate the minimal occlusive pressures required by the patient to achieve coaptation.

The continence producing cuff also includes a super-expansive membrane formed therein having a spring-like memory and being adapted to accommodate a distension of the bowel, such as that which may be caused by a fecal impaction. The extensible membrane has one or more apertures formed therein, the size and number of which apertures establishing a minimum threshold pressure at which the membrane first begins to stretch in response to a distension of the bowel.

DESCRIPTION OF THE PREFERRED EMBODIMENT

Figure 1:
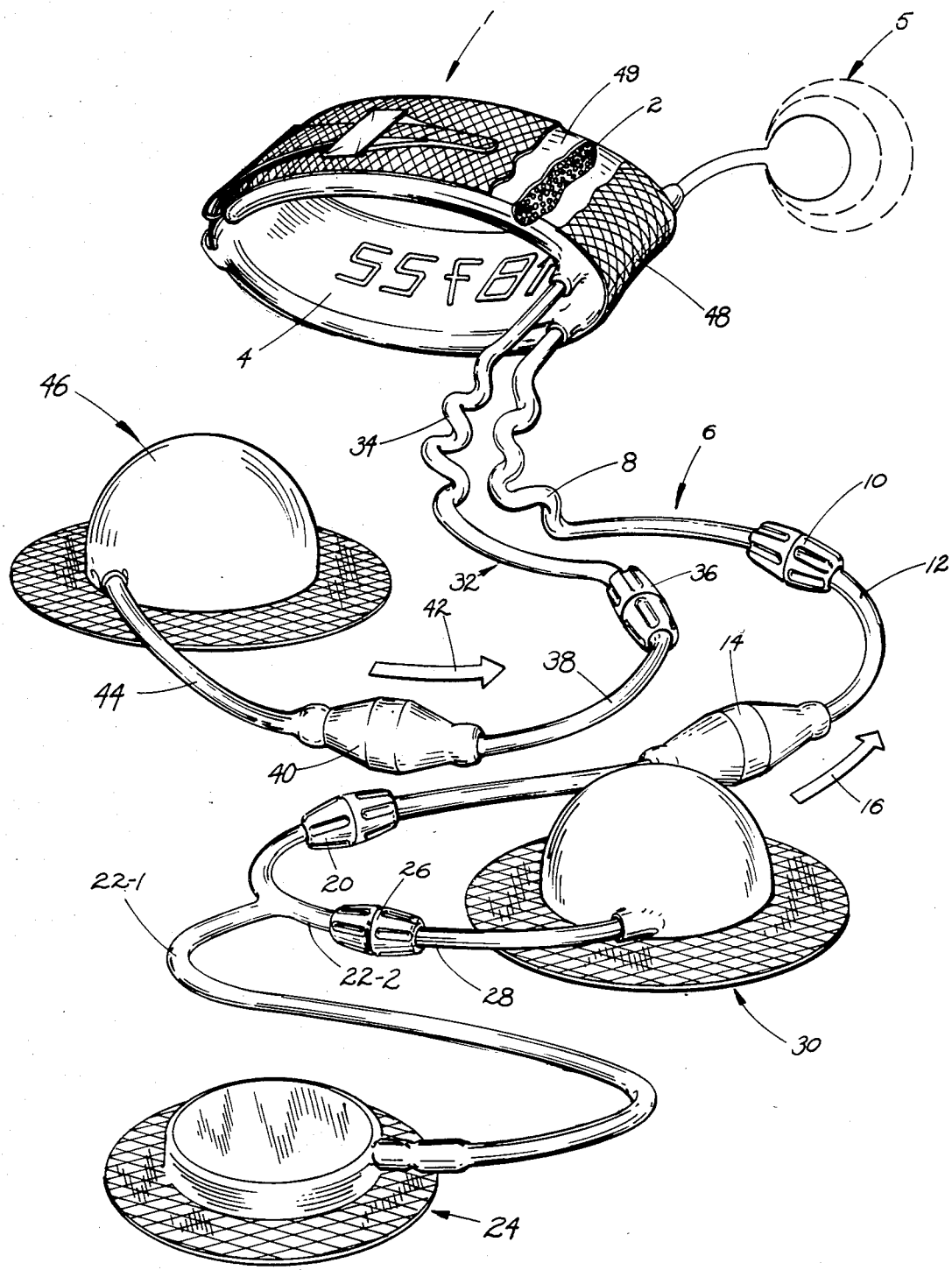
FIG. 1 is a front elevation of the gastrointestinal sphincter and the single, continuous fluidic circuit thereof which form the present invention.

The elastofluidic, gastrointestinal sphincter which forms the present invention and the single, continuous fluidic circuit thereof which permits the sphincter to be tailored to the tissue requirements of the patient are best described while referring initially to FIG. 1 of the drawings. The sphincter includes a generally flat, continence producing occlusion cuff 1 having a body formed from a low durometer, biocompatible, capsule initiating elastomeric material, such as silicone, polyurethane, or the like. In the particular embodiment to be described, the occlusion cuff 1 is adapted to embrace and occlude a lumen, such as, for example, the bowel of a patient who has undergone a colostomy and whose sphincter ani muscle has been removed by surgery to remedy a cancer of the colon. However, it is also to be understood that the present sphincter is also applicable to any other suitable lumen, such as the urethra, the esophagus, a vein, an artery or the vas deferins.

Since the details of continence producing occlusion cuff 1 will be explained when referring to FIG. 4, only a brief description of occlusion cuff 1 is provided hereat. Occlusion cuff 1 includes an exterior layer 48 which is fabricated with a silicone impregnated reinforcing surgical mesh. A non-reinforced interior layer 49 of cuff 1 surrounds a continuous, hollow, expansible chamber 2 which is adapted to be filled with a fluid such that occlusive pressures can be occasionally and variably generated to achieve minimum pressure coaptive continence. A fluid by which to fill the chamber 2 of occlusion cuff 1 may be a low viscosity, isotonic, radio-opaque fluid. During sphincter manufacture, chamber 2 is initially filled with a minimal volume of fluid so as to displace air and other gases therefrom. As will be disclosed hereinafter, the flat occlusion cuff 1 is positioned by a physician during implant surgery so as to articulate a patient's bowel and thereby selectively and variably control occluding and relaxing the bowel to promote or obturate the movement of fecal material therethrough.

Occlusion cuff 1 may include a plate containing x-ray opaque serialization indicia 4 which is typically fabricated from gold, platinum, tantalum, or the like, to provide suitable identifying information for purposes of quality assurance and manufacturing traceability. An expansible pressure sensor and indicator 5 receives the x-ray opaque fluid from the hollow chamber 2 of occlusion cuff 1 so as to be able to provide a visual indication of the fluid generated pressure therewithin. The information provided by sensor-indicator 5 may be interpreted by a nomograph (not shown) to indicate the occlusive pressures being applied to the patient's bowel.

Also communicating with the hollow chamber 2 of occlusion cuff 1 is a primary, fluid filled path 6. Primary fluid path 6 includes tubing which is preferably manufactured from a high durometer, bicompatible material, such as silicone or polyurethane. More particularly, a first section of tubing 8 extends between an inlet/outlet of occlusion cuff 1 and a tube connector 10 arranged in the primary fluid path 6. The first section of tubing 8 may be fabricated as a continuous series of extensible, shock absorbing and kink-resistant helically wound rings which provide a force damping characteristic to insulate delicate tissue and inherent length adjustment to accommodate post-operative patient movement after sphincter implantation. A second section of tubing 12 of the primary fluid path 6 extends between connector 10 and a normally closed, manually manipulatable flow control valve 14. Flow control valve 14 is of the check valve type which permits fluid flow in a single direction (in the direction of arrow 16) but opposes fluid flow in an opposite direction. Although flow control valves of this general type are well known and commercially available, one such valve which is particularly suitable for application herein is described in copending patent application Ser. No. 574,596 filed Jan. 27, 1984.

A third section of tubing 18 of primary fluid path 6 extends between flow control valve 14 and a tube connector 20. A fourth tubing section of primary fluid path 6 has a Y-shaped configuration and extends from connector 20 to each of a remote physician control port 24 (via physician access tubing 22-1) and a tube connector 26 (via tubing section 22-2). The physician control port 24 will be described in detail hereinafter when referring to FIG. 5 of the drawings. A fifth section of tubing 28 extends between connector 26 and a patient controlled, hemispheric fluid reservoir-actuator 30. The reservoir-actuator 30 will be described in greater detail hereinafter when referring to FIGS. 6 and 7 of the drawings.

Also communicating with the hollow chamber 2 of occlusion cuff 1 is a secondary fluid filled path 32. Secondary fluid path 32 includes tubing which is manufactured from the same biocompatible material used to fabricate the tubing of primary fluid path 6. More particularly, a first section of tubing 34 of secondary fluid path 32 extends between another inlet/outlet of occlusion cuff 1 and a tube connector 36. Like the first tubing section 8 of primary fluid path 6, the first tubing section 34 of secondary fluid path 32 may be formed as a continuous series of extensible, shock absorbing and kink resistant helically wound rings.

A second section of tubing 38 of second fluid path 32 extends between connector 36 and a normally closed, manually manipulatable flow control valve 40. Similar to the flow control valve 14 of primary fluid path 6, flow control valve 40 permits fluid flow in a single direction (e.g. in the direction of arrow 42) but opposes fluid flow in an opposite direction. Therefore, flow control valve 40 may be identical to flow control valve 14. A third section of tubing 44 extends between flow control valve 40 and a patient controlled hemispheric fluid reservoir-actuator 46. Like the reservoir-actuator 30 arranged in primary fluid path 6, the reservoir-actuator 46 arranged in secondary fluid path 32 will be described in greater detail when referring to FIGS. 6 and 7 of the drawings.

Figure 2:
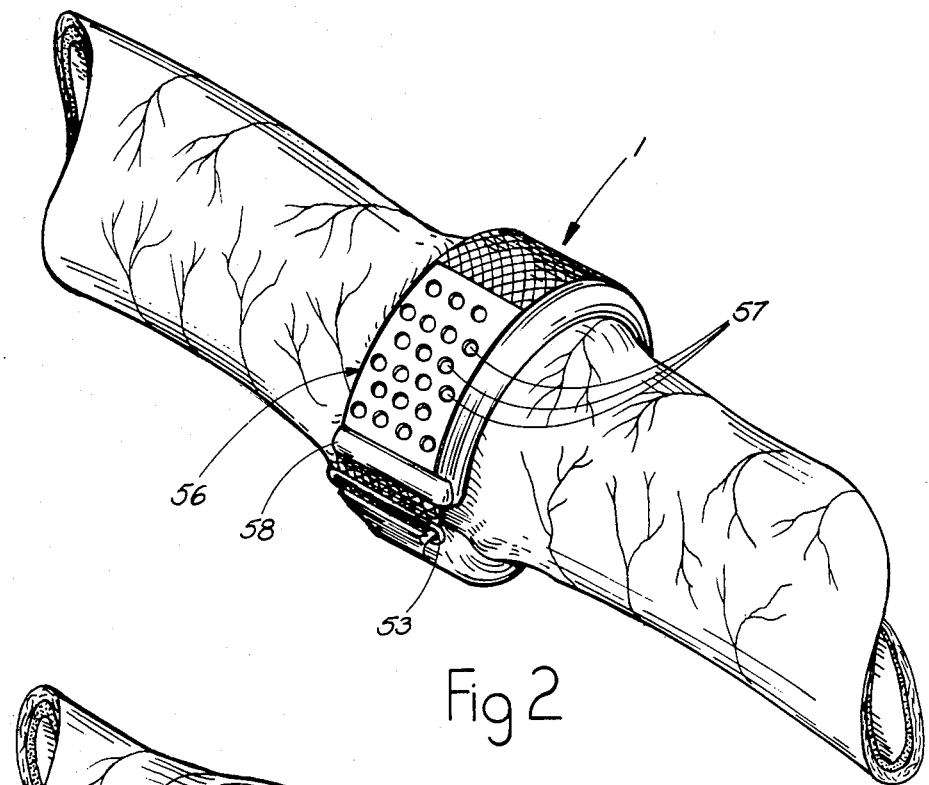
FIG. 2 shows the present sphincter surrounding a patient's bowel.
Figure 3:
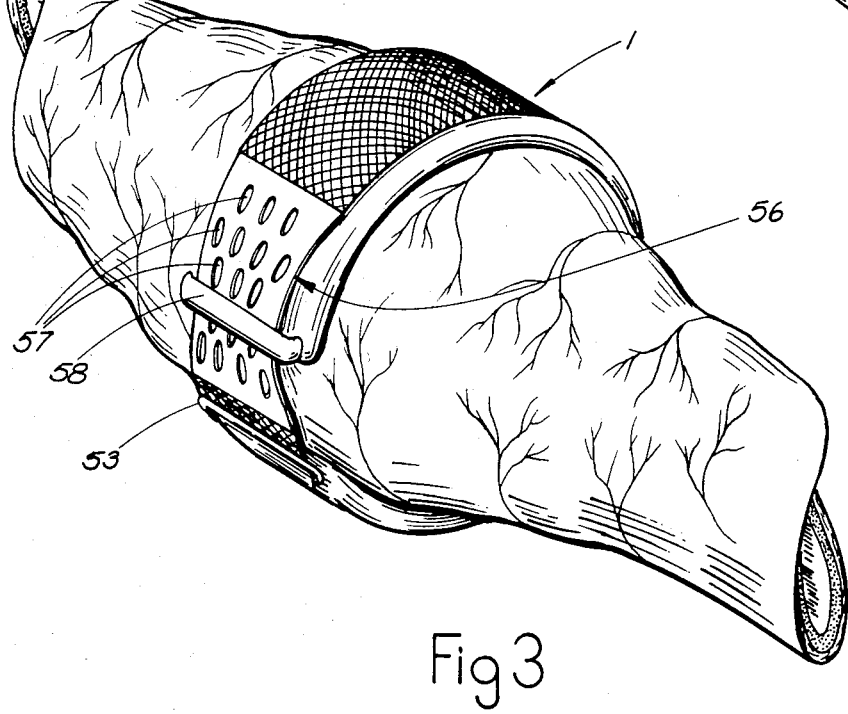
FIG. 3 shows the sphincter of FIG. 2 and a super-expansive area thereof for accommodating a distension in the patient's bowel, such as that caused by fecal impaction.
Figure 4:
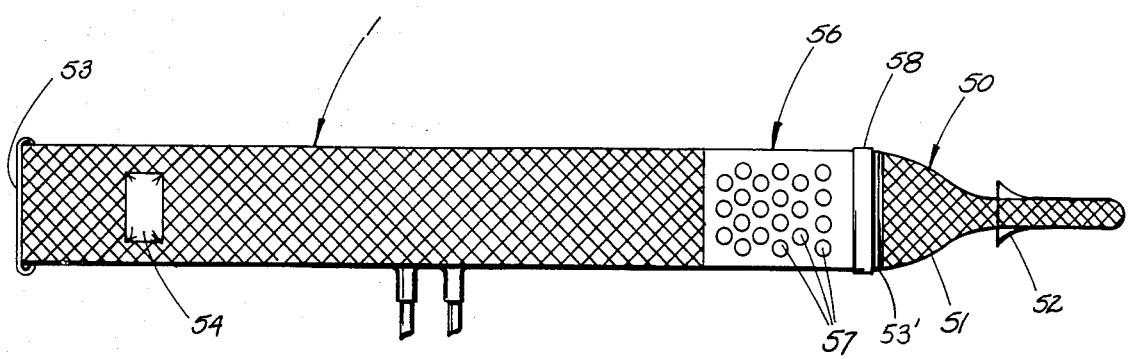
FIG. 4 shows the details of the continence producing occlusion cuff which forms the sphincter of FIG. 1.

Details of the continence producing occlusion cuff 1 are now described while referring concurrently to FIGS. 2, 3 and 4 of the drawings. As previously indicated, and as is best shown in FIG. 4, the occlusion cuff 1 comprises a generally flat, hollow tensile resistant member. A tapered distal aspect 50 of solid cross section is coextensively formed with occlusion cuff 2 at one end thereof. A narrow locking ridge 53' extends across the occlusion cuff at the interface of the distal aspect 50 and the flat occlusion cuff member. The distal aspect 50 comprises a flexible, surgical mesh reinforced locking strap 51 having a delta-shaped locking tab 52 projecting therefrom. Extending from the end of occlusion cuff 1 opposite distal aspect 50 is a metal retaining clip 53. A locking loop 54 is positioned adjacent retaining clip 53.

During implant surgery, the physician secures the occlusion cuff 1 around the patient's bowel (as best shown in FIG. 1) by pulling the locking stray 51 of distal aspect 50 under the retaining clip 53 and through the locking loop 54 such that the locking ridge 53' is engaged and retained by clip 53 and the locking tab 52 is received by locking loop 54. The clip 53 and ridge 53' cooperate as a locking mechanism to prevent the accidental loosening or disengagement of occlusion cuff 1 from the patient's bowel. The dimensions of locking tab 52 relative to locking loop 54 are chosen to prevent the unintended release of tab 52 from loop 54. Thus, tab 52 and loop 54 cooperate as a redundant locking mechanism (with clip 53 and ridge 53') to ensure against the inadvertent loosening or removal of occlusion cuff 1 from the patient's bowel.

An important feature of continence producing occlusion cuff 1 is the inclusion of a resilient, super-expansive area 56. In the embodiment illustrated, super-expansive area 56 is located between the flat, tensile resistant member of occlusion cuff 1 and the distal aspect 50. More particularly, super-expansive area 56 comprises an extensible membrane having a spring-like memory. The membrane is provided with an array of apertures 57 extending therethrough. Although the apertures 57 illustrated in FIGS. 2-4 are circular, it is to be understood that any other suitable aperture configuration, such as rectangular windows, elongated slits, and the like, may be substituted therefor. A lateral guide clip 58 is located across occlusion cuff 1 at the interface of membrane 56 and distal aspect 50.

In FIG. 2 of the drawings, the continence producing occlusion cuff 1 is shown embracing an intestinal lumen (e.g. a bowel). The occlusion cuff 1 is in a non-distended condition, such that super-expansive membrane 56 is relaxed relative to the position of guide clip 58, whereby the adjusting clip 53 and guide clip 58 ends of cuff 1 are located adjacent one another. In FIG. 3 of the drawings, the bowel is impacted. Occlusion cuff 1 is now shown in a distended condition, such that extensible, super-expansive membrane 56 is stretched beyond guide clip 58, whereby the adjusting clip 53 and guide clip 58 ends of cuff 1 are separated from one another. Accordingly, and by virtue of the present invention, the occlusion cuff 1 is adapted to accommodate a distension of a patient's bowel corresponding to the separated distance between the adjusting clip and guide clip ends of cuff 1 when super-expansion membrane 56 is stretched therebetween. When the impacted bowel regains its normal size (of FIG. 2), the guide clip 58 ensures that the adjusting clip and guide clip ends of cuff 1 will return to their original adjacent alignment with one another.

The area of the apertures 57 formed in membrane 56 establishes the threshhold pressure level at which the expansion of membrane 56 begins. That is, the greater the total area of apertures 57, the smaller is the expansive pressure which needs to be exerted by the impacted bowel on occlusion cuff 2 before membrane 56 can be stretched past positioning clip 58. Hence, by selecting a particular number and dimension of apertures 57, the pressure-expansion characteristics of occlusion cuff 1 can be tailored to the tissue requirements of the patient.

Figure 5:
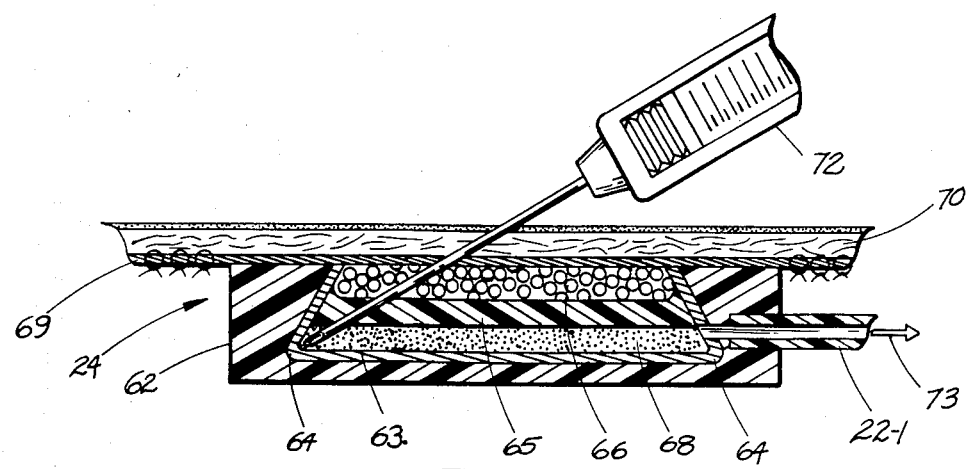
FIG. 5 is a cross section of the physician control port which is located in the fluid circuit of FIG. 1.

The physician control port 24 of FIG. 1 is now described in detail while referring to FIG. 5 of the drawings. Physician control port 24 comprises an exterior body 62 formed from a relatively high durometer, bicompatible material, such as silicone, polyurethane, or the like. Located at the interior of control port 24 is a hollow, metallic housing 63 having a canted shoulder 64 extending therearound. A high durometer membrane 65 extends across the hollow interior of physician control port 24 so as to establish upper and lower control port compartments 66 and 68. During sphincter manufacture, the upper compartment 66 is filled with a self-healing polymer gel, and the lower compartment 68 is filled with a (e.g. low viscosity, isotonic radio-opaque) fluid. The fluid filled compartment 68 communicates with a section of tubing 22-1 from the primary fluid path 6 of FIG. 1. A silicone impregnated, reinforcing surgical mesh 69 is connected across the physician control port 24 and provides a surface by which to permit a physician to surgically attach (e.g. by means of sutures) the control port to the subcutaneous tissue 70 of the patient. The physician control port 24 may be implanted at any suitably accessible location, such as the inguinal area of the patient. However, it is desirable to locate control port 24 remotely from the fluid reservoir-actuators 30 and 46, so as to avoid damage thereto during the soon-to-be-described physician actuation of control port 24.

In the event that sufficient patient initiated occlusive pressure cannot be generated to achieve coaptive continence (by means of actuating the primary and secondary fluid reservoir-actuators 30 and 46 of FIG. 1), the physician may continuously and accurately increase the maximum available occlusive pressure to be applied by the continence producing occlusion cuff 1 to the patient's bowel. More particularly, the physician inserts the tip of a syringe 72 containing an additional supply of fluid through the self-healing polymer gel 66 and membrane 65 into the fluid filled compartment 68 of control port 24. The canted shoulder 64 of control port 24 acts as a self-locating stop for automatically receiving and positioning the tip of syringe 72. Fluid filled compartment 68 is then percutaneously infused with a minimum additional volume of fluid, whereby to force a supply of existing fluid from compartment 68 into tubing section 22-1 (in the direction of arrow 73) and through the primary fluid path 6 of FIG. 1. A carefully controlled amount of fluid is introduced into the primary fluid path 6 to cause an increased inflation of the fluid filled chamber 2 of occlusion cuff 1, until the minimum increased occlusive pressure necessary to achieve coaptive continence is generated. The physician then withdraws the syringe, whereupon the polymer gel within compartment 66 acts to heat the remaining puncture wound and thereby minimizes possible leakage from and damage to physician control port 24.

Figure 6:
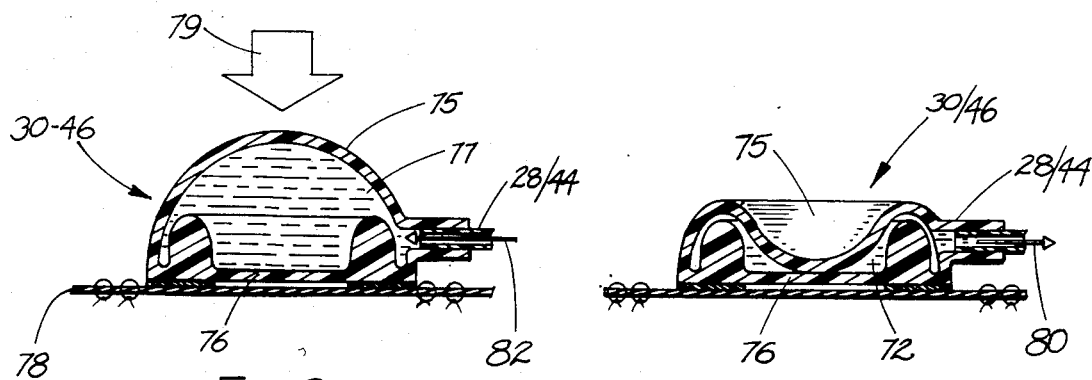
FIGS. 6 and 7 are cross sections of a fluid reservoir in expanded and compressed conditions, respectively, which reservoir is located in the fluid circuit of FIG. 1.
Figure 7:
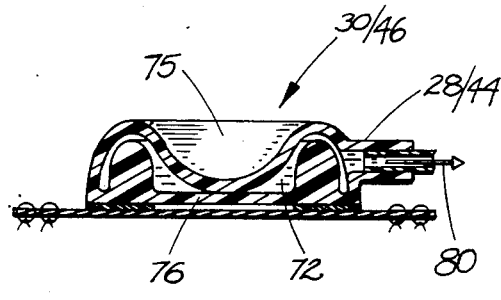

The identically constructed primary and secondary fluid reservoir-actuators 30 and 46 of FIG. 1 are now described while referring to FIGS. 6 and 7 of the drawings. Each reservoir-actuator 30 and 46 comprises a hemispheric outer actuator body 75 which is coextensively formed with an inner locating ring 76. It is to be understood that the hemispheric shape of actuator body 75 is not to be regarded as a limitation of this invention, and other suitable shapes may be substituted therefor. The outer body 75 and inner locating ring 76 of reservoir-actuators 30 and 46 are formed from a suitable biocompatible material, such as silicone, polyurethane, or the like. The hemispheric actuator body 75 is constructed so as to be both flexible and tear resistant. The inner locating ring 76 is constructed to enable a patient to manually locate the reservoir-actuator while in situ. The hemispheric outer actuator body 75 is disposed over and around the inner locating ring 76 so as to form a hollow reservoir 77 which is filled with a (e.g. low viscosity, isotonic, radio-opaque) fluid. Fluid filled reservoir 77 communicates with the primary and secondary fluid paths 6 and 32 of FIG. 1 by way of respective tubing sections 28 and 44. A silicone impregnated, reinforcing surgical mesh 78 is connected across each fluid reservoir-actuator 30 and 46 to provide a surface by which to permit a physician to surgically attach (e.g. by means of sutures) the reservoir-actuator to the subcutaneous tissue of the patient. By way of example, the fluid reservoir-actuators 30 and 46 are located so as to be manually accessible, such as at the anterior ileal crest of the patient.

In the event that the patient wishes to increase the occlusive pressures to be applied from the occlusion cuff to his bowel to achieve coaptive continence, he first locates one of the primary or secondary fluid reservoir-actuators 30 or 46 by means of the locating ring 76 thereof. The patient then depresses the flexible hemispheric actuator body 75 (in the direction indicated by the arrow 79 of FIG. 6), whereby to compress the fluid filled reservoir 77 (best shown in FIG. 7) and thereby force a supply of fluid from reservoir 77 into tubing section 28 or 44 (in the direction indicated by arrow 80 of FIG. 7) and through the primary or secondary fluid path 6 or 32. Accordingly, fluid is transmitted to the occlusion cuff in order to cause the chamber thereof to inflate. However, the patient may have to actuate both actuator-reservoirs 30 and 46 (in the manner just described) to cause a sufficient inflation of the occlusion cuff chamber and a corresponding occlusive pressure necessary to achieve coaptive continence.

By virtue of the presently disclosed sphincter and the single, continuous fluidic circuit thereof (best illustrated in FIG. 1), variable occlusive pressure levels can be selectively established for applying diametric compression to a bowel for holding a patient continent. That is, when the patient controlled, primary fluid reservoir-actuator 30 is actuated, the primary fluid path 6 transmits sufficient fluid therethrough by which to partially inflate the hollow chamber 2 of continence producing occlusion cuff 1 and thereby achieve a first (i.e. fecal continence) occlusive pressure level. At such fecal continence pressure level, methane gas may pass through the patient's colon. However, the passage of fecal material throught the colon is otherwise impeded. When the patient controlled, secondary fluid reservoir-actuator 46 is also manually actuated, the secondary fluid path transmits additional fluid therethrough by which to further inflate the chamber 2 of occlusion cuff 1 so as to achieve a second (i.e. flatus continence) occlusive pressure level. At such flatus continence pressure level, neither methane gas nor fecal material may pass through the colon. The presence of physician control port 24 permits limited additional fluid to be transmitted to occlusion cuff 1 via primary fluid path 6 to further increase the inflation of chamber 2 and thereby achieve a maximum occlusive pressure level, according to the tissue requirements of the patient.

Occassionally, however, the patient wishes to discharge both gaseous and fecal matter through his bowel. Therefore, it periodically becomes necessary to reduce the occlusive pressures being applied to the patient's bowel by the fluid filled chamber 2 of occlusion cuff 1. Accordingly, one or both of the primary or secondary flow control valves 14 or 40 are manually manipulated and thereby opened (in a manner described in the aforementioned patent application Ser. No. 574,596 filed Jan. 27, 1984), whereby to shrink the chamber 2 of occlusion cuff 1 and permit fluid to return to the primary and/or secondary reservoir-actuators via the respective fluid paths 6 and 32 (in a direction represented by the arrow 82 of FIG. 6). The opening of both flow control valves 14 and 40 causes the fluid filled occlusion cuff 2 to shrink to its original and unexpanded size, the reservoir-actuators 30 and 46 to inflate to their original, expanded size, and the occlusive pressures being applied to the patient's bowel to be minimized. Of course, only one of the primary or secondary flow control valves 14 or 40 need be opened to cause a partial shrinking of the fluid filled chamber and a reduction in the occusive pressures being applied thereby. An occassional reduction in the occlusive pressure is also desirable to maximize circulatory blood flow through the bowel and reduce the possibility of ischemia, erosion and/or necrosis.

It is to be recognized that the aforementioned variable occlusive pressure levels are achieved by means of a single, multi-access occlusion cuff chamber 2 which communicates with each of the primary and secondary fluid paths 6 and 32. It is also to be recognized that unlike conventional sphincters, the presently disclosed sphincter may be regarded as a dual purpose, multi-threshhold device. That is, while the continuous fluidic circuit of FIG. 1 is adapted to establish variable occlusive pressure levels to articulate a bowel and hold a patient continent, the super-expansive membrane 56 of FIGS. 2 and 3 provides the occlusion cuff 1 with the ability to accommodate a distended colon, such as that caused by fecal impaction. The threshhold pressure level at which the expansion of membrane 56 begins can be selectively controlled, depending upon the dimension of the apertures 57 formed therein.

Figure 8:
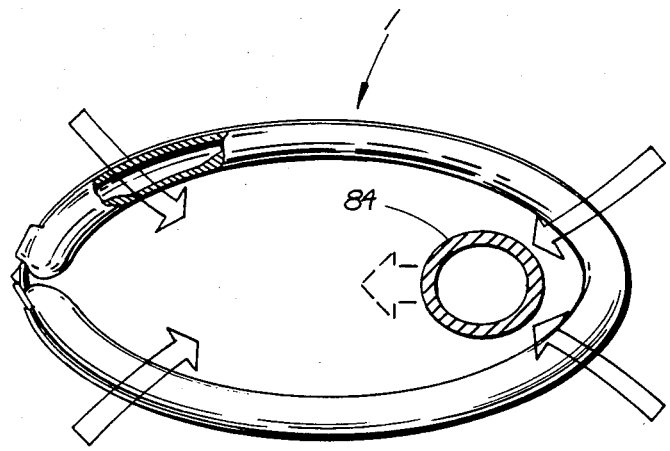
FIGS. 8-10 illustrate an automatic, self centering feature of the present sphincter for optimally positioning the patient's bowel so that coaptive continence may be achieved by means of diametric compression.
Figure 9:
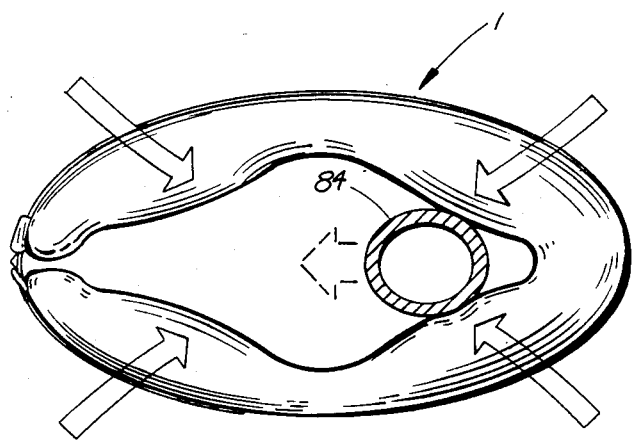
Figure 10:
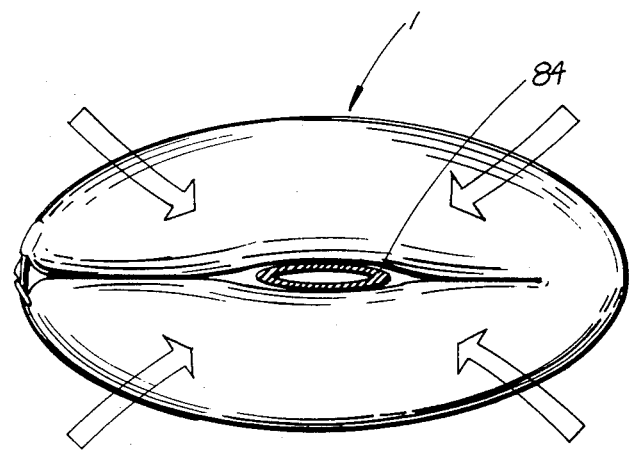

An automatic, self-centering feature of the present invention is briefly explained while concurrently referring to FIGS. 8, 9 and 10 of the drawings. In FIG. 8, an uninflated occlusion cuff 1 is closed around a lumen 84 (e.g. bowel) of a patient. As fluid is conveyed to the continence producing occlusion cuff 1, the thin wall sections of the hollow chamber thereof begin to expand first (FIG. 9), whereby to automatically relocate the bowel towards the center of the cuff and thereby avoid a possible pinching of the bowel. With the chamber of occlusion cuff 1 fully inflated (FIG. 10), the bowel will be centrally and optimally disposed, so as to receive diametric occlusive pressure by which to reliably and efficiently achieve coaptive continence.

It will be apparent that while a preferred embodiment of the invention has been shown and described, various modifications and changes may be made without departing from the true spirit and scope of the invention. By way of example, although the fluid paths 6 and 32 have been designated primary and secondary, respectively, this is not to be regarded as a limitation of the invention. It is therefore to be understood that either fluid path 6 or 32 may be regarded as primary or secondary. Likewise, and since each of the fluid paths 6 and 32 communicate with the hollow chamber 2 of occlusion cuff 1 via a single, continuous fluidic circuit, the fluid reservoir-actuators 30 and 46 may be actuated in any order to establish the variable occlusive pressure levels, whereby to achieve coactive continence. What is more, the physician control port 24 may communicate with occlusion cuff 2 via either the primary or secondary fluid path 6 or 32.

Having thus set forth a preferred embodiment of the present invention what is claimed is:

1. A prosthetic sphincter for surgical implantation to apply occlusive pressures to a patient's lumen for achieving coaptive continence, said sphincter comprising:
　　an occlusion cuff surrounding the lumen and having an expandable chamber thereof for engaging and articulating the lumen;
　　a first fluid filled path communicating with said expandable chamber;
　　a second fluid filled path communicating with said expandable chamber; and first and second fluid filled reservoirs respectively interconnected with said first and second fluid paths by which to selectively deliver a supply of fluid under pressure via either one or both of said paths to said expandable chamber for controlling the expansion of said chamber and varying the occlusive pressures being applied to the lumen for achieving coaptive continence, each of said reservoirs being surgically implanted at a manually accessible area of the patient and having respective flexible surfaces to be manually depressed to compress its associated reservoir and force fluid therefrom and into a corresponding fluid path for delivery to said expandable chamber, such that the successive compression of the first and then the second of said reservoirs variably increasing the occlusive pressure being applied to said lumen from a first to a second pressure level.

2. The prosthetic sphincter recited in claim 1, wherein the expandable chamber of said occlusion cuff and the first and second fluid paths are interconnected as a single, continuous fluid circuit.

3. The prosthetic sphincter recited in claim 2, wherein each reservoir also has a rigid locating means by which a patient can locate said reservoir in order that said flexible surface thereof can be manually depressed.

4. The prosthetic sphincter recited in claim 3, wherein said means to deliver a supply of fluid to said expandable chamber also includes a fluid filled, physician actuated port, said fluid filled port being surgically implanted at a manually accessible area of the patient and interconnected with at least one of said first and second fluid paths, said fluid filled port having a region in which to receive a fluid filled syringe so that an additional supply of fluid can be introduced to said port to force existing fluid therefrom and into said corresponding fluid path for delivery to said expandable chamber.

5. The prosthetic sphincter recited in claim 4, wherein said fluid filled port also has a puncture healing region interfaced with the region in which to receive the syringe, said puncture healing region healing any punction wound remaining after the withdrawal of the syringe and preventing leakage of fluid from said port.

6. The prosthetic sphincter recited in claim 1, including fluid pressure indicating means communicating with the expandable chamber of said occlusion cuff for receiving fluid therefrom and providing an indication of the fluid pressure within said chamber.

7. The prosthetic sphincter recited in claim 1, wherein said occlusion cuff includes an extensible region formed therein, said extensible region having a spring-like memory to accommodate a distension of the patient's lumen when said occlusion cuff is located therearound.

8. The prosthetic sphincter recited in claim 7, wherein said extensible region has one or more apertures formed therein, the size and number of said apertures establishing a minimum threshhold pressure level at which said extensible region first begins to stretch in response to a distended lumen.

9. The prosthetic sphincter recited in claim 1, wherein said occlusion cuff has first and second ends to be releasably connected together to surround the patient's lumen, one of said cuff ends having a raised portion and the other of said cuff ends having a retaining clip, said raised portion and retaining clip cooperating to form interlocking means to connect said first and second cuff ends together when the raised portion of said first cuff end is pulled through the retaining clip of said second cuff end.

10. The prosthetic sphincter recited in claim 9, wherein said first cuff end includes a tab projecting therefrom and said second cuff end includes a locking loop, said projecting tab and said locking loop cooperating to form an additional, redundant interlocking means to connect said first and said second cuff ends together when the projecting tab of said first cuff end is pulled through the locking loop of said second cuff end.

11. The prosthetic sphincter recited in claim 1, wherein said means to deliver a supply of fluid to said expandable chamber includes first and second check valves respectively interconnected with said first and second fluid paths to control the flow of fluid therethrough.

12. A prosthetic sphincter for surgical implantation, said sphincter including a continence producing occlusion cuff being relatively inextensible and resistant to elongation in response to tensile stretching forces and surrounding a patient's lumen to apply occlusive pressure for occluding and relaxing the lumen and thereby controlling the movement of material therethrough, said occlusive cuff having an expandable chamber to embrace the lumen, said sphincter further comprising:

means to selectively deliver fluid to said expandable chamber to controllably expand said chamber and thereby produce occlusive pressure for achieving coaptive continence, and relatively extensible membrane means subject to variable elongation in response to at least predetermined minimum tensile stretching forces, said membrane means interconnected with said occlusion cuff to increase the inside circumference of said cuff and thereby accommodate a distension of the lumen when said occlusion cuff is positioned therearound.

13. The prosthetic sphincter recited in claim 12, wherein said means to selectively deliver fluid to said expandable chamber comprises a first fluid filled path communicating with said chamber and having a fluid filled reservoir located therein and a second fluid filled path also communicating with said chamber and having a fluid filled reservoir located therein.

14. The prosthetic sphincter recited in claim 13, wherein each of said first and second fluid paths and said expandable chamber are interconnected as a single, continuous fluid circuit.

15. The prosthetic sphincter recited in claim 13, wherein each of said fluid filled reservoirs has a flexible surface which is adapted to be depressed so as to compress said reservoirs and force fluid therefrom into respective fluid paths for delivery to said expandable chamber.

16. The prosthetic sphincter recited in claim 13, wherein said means to selectively deliver fluid to said expandable chamber also comprises at least one fluid filled port interconnected with one of said first or second fluid filled paths and surgically located to be accessible to a fluid filled syringe so that an additional supply of fluid can be introduced to said port to force existing fluid therefrom into said corresponding fluid path for delivery to said expandable chamber.

17. The prosthetic sphincter recited in claim 13, wherein said means to selectively deliver fluid to said expandable chamber also comprises first and second check valves respectively interconnected with said first and second fluid paths to control the flow of fluid therethrough.

18. The prosthetic sphincter recited in claim 12, wherein said extensible means has one or more apertures formed therein, the size and number of said apertures establishing a minimum threshhold pressure level at which said extensible means first begins to stretch in response to a distension of the lumen.

19. A prosthetic sphincter for surgical implantation to apply occlusive pressures to a patient's lumen for achieving coaptive continence, said sphincter comprising:

an occlusion cuff being relatively inextensible and resistant to elongation in response to tensile stretching forces and surrounding the lumen and having an expandable chamber thereof for engaging and articulating the lumen;

a first fluid filled path communicating with said expandable chamber;

a second fluid filled path communicating with said expandable chamber;

first and second fluid filled reservoirs respectively interconnected with said first and second fluid paths and having respective flexible surfaces to be manually depressed to force fluid outwardly therefrom and into a corresponding fluid path for delivery to said expandable chamber for filling said chamber and increasing the occlusive pressure being applied to the patient's lumen such that the successive compression of the first and then the second of said reservoirs variably increases the occlusive pressure being applied to said lumen from a first to a second pressure level;

a fluid filled physician actuated port, said fluid filled port being surgically implanted at a manually accessible area of the patient and interconnected with at least one of said first and second fluid paths, said fluid filled port having a region in which to receive a fluid filled syringe so that an additional supply of fluid can be introduced to said port to force existing fluid therefrom and into said corresponding fluid path for delivery to said expandable chamber; and relatively extensible membrane means subject to variable elongation in response to at least predetermined minimum tensile stretching forces, said membrane means interconnected with said occlusion cuff to increase the inside circumference thereof and thereby accommodate a distension of the lumen when said membrane means and occlusion cuff are positioned therearound.

* * * * *